United States Patent
Payne

(10) Patent No.: US 7,735,486 B2
(45) Date of Patent: Jun. 15, 2010

(54) MEDICAL RESPIRATORY APPARATUS

(75) Inventor: Simon Robert Payne, Surrey (GB)

(73) Assignee: Intersurgical AG, Vaduz (LI)

( * ) Notice: Subject to any disclaimer, the term of this patent is extended or adjusted under 35 U.S.C. 154(b) by 0 days.

(21) Appl. No.: 10/465,924

(22) PCT Filed: Jan. 4, 2002

(86) PCT No.: PCT/GB02/00026

§ 371 (c)(1),
(2), (4) Date: Jan. 21, 2004

(87) PCT Pub. No.: WO02/058770

PCT Pub. Date: Aug. 1, 2002

(65) Prior Publication Data

US 2004/0103893 A1    Jun. 3, 2004

(30) Foreign Application Priority Data

Jan. 6, 2001 (GB) ................................. 0100397.9

(51) Int. Cl.
*A61M 15/00* (2006.01)
*A61M 16/10* (2006.01)

(52) U.S. Cl. ..................... 128/203.12; 128/200.23; 128/205.23; 128/203.15; 600/529; 600/534; 600/538; 600/540; 482/13; 116/109; 116/110; 116/227; 116/228; 206/459.1; 215/230

(58) Field of Classification Search ............ 128/200.23, 128/205.23, 203.12, 203.15; 600/529, 534, 600/538, 540; 482/13; 116/109, 110, 227, 116/228; 206/459.1; 215/230
See application file for complete search history.

(56) References Cited

U.S. PATENT DOCUMENTS

| 1,563,316 | A |   | 12/1925 | Anscombe |
| 2,767,586 | A |   | 10/1956 | Jancosek et al. |
| 3,398,897 | A |   | 8/1968  | Urbanowicz |
| 3,593,712 | A | * | 7/1971  | Weaver et al. ......... 128/200.16 |
| 4,210,155 | A | * | 7/1980  | Grimes ....................... 600/540 |
| 5,052,224 | A |   | 10/1991 | Ford et al. |
| 5,447,248 | A | * | 9/1995  | Rodriguez et al. .......... 215/366 |
| 5,785,178 | A | * | 7/1998  | Kvitrud et al. ........... 206/459.1 |
| 5,984,873 | A | * | 11/1999 | Crumb et al. ............... 600/538 |

FOREIGN PATENT DOCUMENTS

FR    2553511    4/1985
WO    WO 98/19620    5/1998

OTHER PUBLICATIONS

Search Report, GB 0200118.8, Jun. 24. 2002.

* cited by examiner

*Primary Examiner*—Patricia M Bianco
*Assistant Examiner*—Nihir Patel
(74) *Attorney, Agent, or Firm*—Nixon Peabody LLP

(57) ABSTRACT

A medical respiratory apparatus includes a chamber (10) which is at least in part at least translucent. The chamber (10) includes a float member (12) formed of an inert material and contains, in use, a fluid intended for inhalation. The float member (12) is adapted to float upon the fluid intended to be contained within the chamber (10) and has a peripheral dimension adjacent, but less than, the internal peripheral dimension of the chamber (10). At least the outer peripheral surface of the float member (12) has a coloration distinct from that of the fluid to be contained within the chamber such that the level of the fluid within the chamber (10) can be readily observed.

24 Claims, 1 Drawing Sheet

MEDICAL RESPIRATORY APPARATUS

Figure 1:
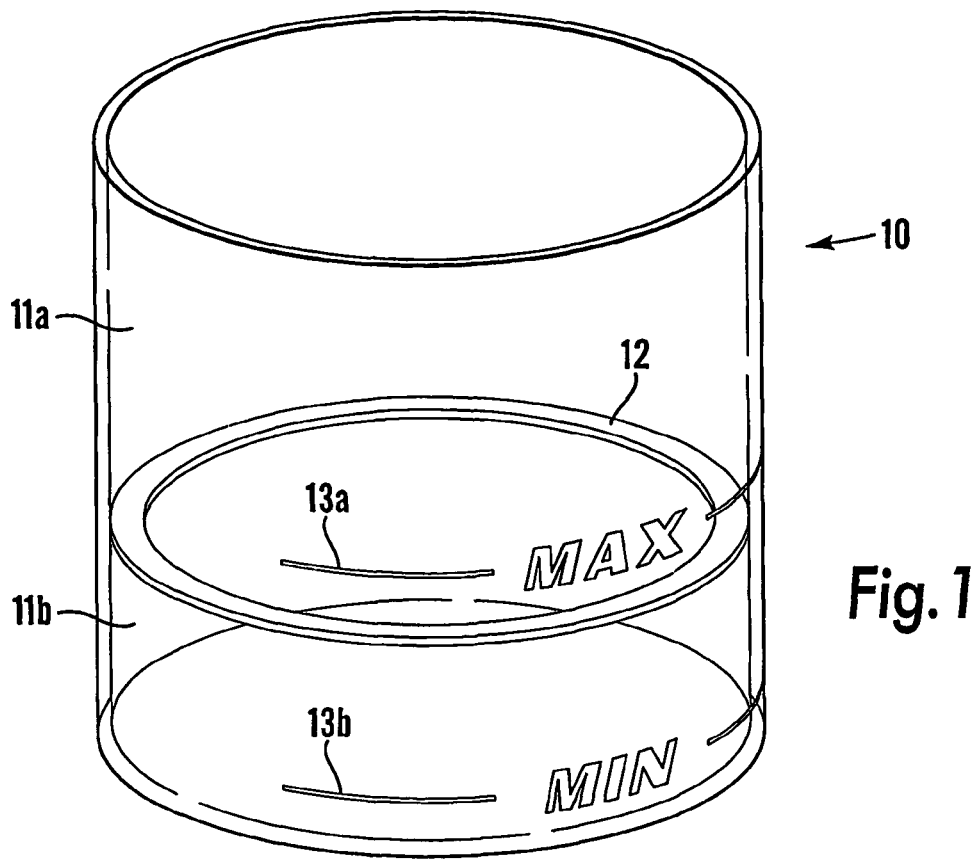

This application is a national stage application under 35 U.S.C. §371 from PCT Application GB02/00026 filed Jan. 4, 2002, which claims priority benefit of Great Britain application 0100397.9 filed Jan. 6, 2001.

FIELD OF THE INVENTION

The invention relates to improvements in medical respiratory apparatus, more particularly, although not exclusively, to nebulisers, humidifiers, combinations thereof and related or ancillary equipment. The invention is particularly concerned with improvements in fluid level indicators in such apparatus.

BACKGROUND OF THE INVENTION

A medical respiratory apparatus such as a nebuliser or humidifier commonly includes a transparent or translucent chamber, containing fluid, usually water or an aqueous solution of a medicament intended for inhalation. In use, the fluid is entrained in a flow of air or other gas which is inhaled by a patient. The level of the fluid in the chamber needs to be instantly visually identified, effectively and efficiently, by the human eye for reasons of efficient and effective operation of the apparatus and in some instances safety. For instance, it may be necessary to ensure that the level of the fluid does not fall below a prescribed minimum or rise above a prescribed maximum. However, such levels can often be indistinct or obscured due to the opaqueness of the chamber material, condensation of fluid on chamber walls, product graphics and labels, or the transparency of the fluid itself.

There have now been devised improvements to medical respiratory apparatus which overcome or substantially mitigate the above-mentioned or other disadvantages of the prior art.

SUMMARY OF THE INVENTION

According to the invention there is provided a medical respiratory apparatus including a chamber which is at least in part at least translucent, the chamber containing, in use, a fluid intended for inhalation, such chamber including a float member formed of an inert material, the float member being adapted to float upon the fluid intended to be contained within the chamber and having a peripheral dimension adjacent, but less than, the internal peripheral dimension of the chamber, at least the outer peripheral surface of the float member having a colouration distinct from that of the fluid to be contained within the chamber, whereby the level of the fluid within the chamber can be readily observed.

The apparatus according to the invention is advantageous primarily in that the float member provides a readily visible and clear indication of the level of fluid within the chamber. This facilitates monitoring of the fluid level and reduces the risk of the fluid level falling below a desired minimum level.

The float member must be of a density and shape such that, when the float member is stationary and not fully submerged in the fluid, the weight of the fluid displaced combined with any upward force exerted on the float member by the surface tension of the fluid is equal to the weight of the float member. For example, the float member may be hollow, of foamed material or, most preferably, the float member is formed in a material of lower density than the fluid.

By "at least translucent" is meant that at least part of the chamber, preferably all of the chamber or all of the peripheral surface of the chamber, is transparent or sufficiently light-transmissive for the float member to be visible. The chamber is preferably transparent.

The chamber may be cylindrical. With such apparatus the overall diameter of the chamber in a humidifier may be in the range 80 mm to 200 mm, eg of the order of 150 mm, and of the chamber in a nebuliser may be in the range 20 mm to 80 mm, eg of the order of 50 mm.

The float member in such apparatus may be formed of a synthetic plastics material such as a polyolefin, for example polypropylene or polyethylene. The float member is preferably formed by moulding, for example blow moulding, rotational moulding or, most preferably, injection moulding.

The colouration may be provided by forming the float member in a pigmented plastics material, or by painting or otherwise coating the float member after moulding.

The float member is preferably formed as a ring. Most preferably, the float member is flat or substantially flat, the width of the material making up the float member being greater than its depth. The float member may commonly have a cross-sectional thickness of the order of 1.5 to 2 mm. In a particularly preferred embodiment, the float member comprises a substantially flat ring having an overall diameter slightly less than the internal diameter of the chamber, the ring material having a thickness of between 0.5 and 3 mm and a width of between 3 and 20 mm, more preferably between 3 and 10 mm.

Preferably the colouration referred to hereinabove should be such as to ensure that the float member is readily visible to a normally sighted person, but also to a partially sighted person or a person with colourblindness. The colouration should therefore preferably be of a colour and tone which is readily distinguishable by such persons.

The foregoing and further features of the invention may be more readily understood from the following description of a preferred embodiment thereof, by way of example only, with reference to the accompanying drawings.

BREIF DESCRIPTION OF THE DRAWINGS

Figure 2:
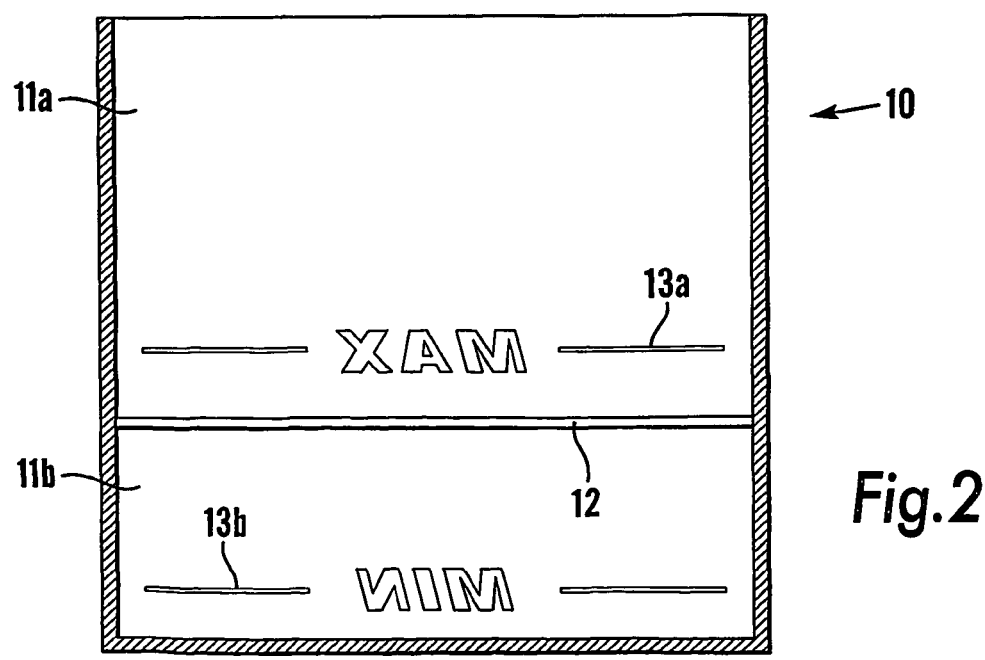

FIG. 1 shows a perspective view of a chamber, for use in a respiratory apparatus, including a float member, and FIG. 2 is a side sectional view of the apparatus of FIG. 1.

DETAILED DESCRIPTION OF THE INVENTION

Referring now to the drawings there is shown a chamber 10 which may be included in a humidifier or nebuliser. The chamber 10 has an empty upper portion 11a and a lower portion 11b containing a fluid which may be water or an aqueous solution of a medicament intended for inhalation. An annular float member 12 is located upon the upper surface of the fluid in the lower portion 11b so as to rise and fall with the level of such fluid between an indicated maximum level 13a and a minimum level 13b which are formed or etched or otherwise formed around the wall of chamber 10.

The chamber 10 is formed of a transparent or at least translucent material such that the level of the fluid contained therein can be clearly observed by the human eye. The float member 12 is coloured to provide an enhanced level indication of the upper level of the fluid contained in the lower portion 11b of chamber 10.

In a typical nebuliser the chamber 10 would have a diameter of the order of 20 mm to 80 mm, eg 35 mm or 50 mm, and in a humidifier of the order of 80 mm to 200 mm, eg 110 mm or 150 mm. With such apparatus the annular float member 12 would typically have a cross-sectional thickness of the order of 1.5 mm to 2 mm.

The float member 12 must float upon the fluid to be contained in the chamber 10. For example, the float member 12 may be formed in a material of lower density than such fluid. Furthermore the float member 12 must be inert with respect to such fluid. The float member 12 is ideally formed of a synthetic plastics material, such as polypropylene, formed by injection moulding. The float member 12 should be coloured to be distinct so as to be clearly visible to the human eye having regard to any obscurities of the wall of chamber 10 and any partial sightedness or colourblindness of the observer. Hence the float member may be coloured dark red or some alternative dark hue having a good colour/tonal contrast against a light coloured fluid in the chamber 10. Alternatively, the float member may be light coloured having a good colour/tonal contrast against a dark coloured fluid in the chamber 10.

In the embodiment described hereinbefore the chamber 10 is shown as cylindrical but could have any tubular cross-section such as square, rectangular or elliptical. The float member 12 preferably has a shape conforming to the internal shape of the chamber 10.

The float member 12 is shown as an annular ring but could be in a form spanning the surface of the fluid contained therein, provided at least the outer peripheral surface has a distinctive colour and that sufficient of the surface of the fluid is exposed to permit entrainment of fluid in the atmosphere above it.

Furthermore in an arrangement where the fluid containment chamber 10 is not readily viewable a separate level indicating tube or chamber could be attached at the lower end thereof, with fluid interconnection therewith, and the float member 12 contained therein. In such a case, it may not be necessary for fluid in the level indicating tube or chamber to be entrained in the atmosphere above it and so the float member may cover the whole surface of the fluid in the level indicating tube or chamber. The float member in such a case may, for instance, take the form of a disc or membrane.

The invention claimed is:

1. A medical respiratory apparatus including a cylindrical respiratory chamber which is at least in part at least translucent, the chamber containing, in use, a fluid intended for inhalation that is water or an aqueous solution of a medicament intended for inhalation, such chamber including a float member formed of an inert material, the float member being a ring adapted to float upon the water or aqueous solution intended for inhalation such that sufficient of the surface of the water or aqueous solution is exposed to permit entrainment of the water or aqueous solution intended for inhalation in the atmosphere above it, the float member having a shape conforming to the internal shape of the chamber and an overall diameter slightly less than the internal diameter of the chamber, at least the outer peripheral surface of the float member having a coloration distinct from that of the water or aqueous solution to be contained within the chamber, whereby the level of the water or aqueous solution within the chamber can be readily observed.

2. A medical respiratory apparatus as claimed in claim 1, wherein the float member is formed in a material of lower density than the water or aqueous solution to be contained within the chamber.

3. A medical respiratory apparatus as claimed in claim 1, wherein the whole of the chamber or the peripheral surface of the chamber is at least translucent.

4. A medical respiratory apparatus as claimed in claim 1, wherein at least part of the chamber is transparent.

5. A medical respiratory apparatus as claimed in claim 1, wherein the medical respiratory apparatus is a humidifier.

6. A medical respiratory apparatus as claimed in claim 5, wherein the chamber has a diameter of between 80 and 200 mm.

7. A medical respiratory apparatus as claimed in claim 1, wherein the medical respiratory apparatus is a nebulizer.

8. A medical respiratory apparatus as claimed in claim 7, wherein the chamber has a diameter of between 20 and 80 mm.

9. A medical respiratory apparatus as claimed in claim 1, wherein the float member is formed in a synthetic plastics material.

10. A medical respiratory apparatus as claimed in claim 9, wherein the float member is formed in a polyolefin.

11. A medical respiratory apparatus as claimed in claim 9, wherein the float member is formed in polypropylene.

12. A medical respiratory apparatus as claimed in claim 1, wherein the float member is formed by molding.

13. A medical respiratory apparatus as claimed in claim 12, wherein the float member is formed by injection molding.

14. A medical respiratory apparatus as claimed in claim 12, wherein the float member is coated after molding.

15. A medical respiratory apparatus as claimed in claim 1, wherein the float member is formed in a pigmented plastics material.

16. A medical respiratory apparatus as claimed in claim 1, wherein the width of the material making up the float member is greater than its depth.

17. A medical respiratory apparatus as claimed in claim 1, wherein the ring material has a thickness of between 0.5 and 3 mm.

18. A medical respiratory apparatus as claimed in claim 1, wherein the ring material has a width of between 3 and 20 mm.

19. A medical respiratory apparatus as claimed in claim 1, wherein the ring material has a width of between 3 and 10 mm.

20. A medical respiratory apparatus as claimed in claim 1, wherein the float member has a cross-sectional thickness of between 1.5 to 2 mm.

21. A medical respiratory apparatus as claimed in claim 1, wherein the coloration is a color and tone such that the float member is readily visible to a partially sighted person or a person with colorblindness.

22. A medical respiratory apparatus as claimed in claim 1, wherein the float member is substantially flat.

23. A medical respiratory apparatus as claimed in claim 1, wherein the float member is flat.

24. A nebulizer or humidifier for use with a respiratory device, the nebulizer or humidifier comprising:
 a cylindrical respiratory chamber which is at least in part at least translucent, the chamber containing, in use, a fluid intended for inhalation that is water or an aqueous solution of a medicament intended for inhalation, and
 a float member positioned within the chamber, the float member being formed of an inert material of lower density than the water or aqueous solution intended for inhalation, such that the float member is adapted to float upon the water or aqueous solution intended for inhalation, the float member being a ring that conforms to the internal shape of the chamber and has an overall diameter slightly less than the internal diameter of the chamber such that sufficient of the surface of the water or aqueous solution is exposed to permit entrainment of the water or aqueous solution intended for inhalation in the atmosphere above it, and at least the outer peripheral surface of the float member having a coloration distinct from that of the water or aqueous solution to be contained within the chamber during use, whereby the level of the water or aqueous solution within the chamber can be readily observed.

* * * * *